United States Patent
Gallem et al.

(10) Patent No.: US 7,562,656 B2
(45) Date of Patent: Jul. 21, 2009

(54) AEROSOL MEDICATION INHALATION SYSTEM

(75) Inventors: Thomas Gallem, München (DE); Kevin Grant Gowanlock, London (CA); Robert Carlton Lynch, Apex, NC (US)

(73) Assignee: Hydrate, Inc., Midlothian, VA (US)

( * ) Notice: Subject to any disclaimer, the term of this patent is extended or adjusted under 35 U.S.C. 154(b) by 1030 days.

(21) Appl. No.: 10/943,542

(22) Filed: Sep. 17, 2004

(65) Prior Publication Data

US 2005/0039741 A1 Feb. 24, 2005
US 2006/0011196 A2 Jan. 19, 2006

Related U.S. Application Data

(63) Continuation of application No. 10/137,007, filed on May 2, 2002, now abandoned.

(51) Int. Cl.
*A61M 11/00* (2006.01)
(52) U.S. Cl. .............. 128/200.14; 128/200.22; 128/200.17
(58) Field of Classification Search ............ 128/200.14, 128/200.23, 200.22, 200.17
See application file for complete search history.

(56) References Cited

U.S. PATENT DOCUMENTS

| | | | |
|---|---|---|---|
| 393,369 A | 11/1888 | Hawkins | |
| 2,670,739 A | 3/1954 | McNeill | |
| 3,236,458 A | 2/1966 | Ramis | |
| 3,556,122 A | 1/1971 | Laerdal | |
| 3,643,686 A | 2/1972 | Koegel | |
| 3,809,084 A | 5/1974 | Hansen | |
| 3,809,294 A | 5/1974 | Torgenson | |
| 3,838,686 A | 10/1974 | Szekly | |
| 3,897,779 A | 8/1975 | Hansen | |
| 3,994,421 A | 11/1976 | Hansen | |
| 4,174,712 A | 11/1979 | Moren et al. | |
| 4,182,366 A | 1/1980 | Boehringer | |
| 4,231,375 A | 11/1980 | Boehringer et al. | |
| 4,267,832 A | 5/1981 | Hakkinen | |
| 4,275,722 A | 6/1981 | Sorensen | |
| 4,292,966 A | 10/1981 | Mono et al. | |
| 4,298,023 A | 11/1981 | McGinnis | |
| 4,344,573 A * | 8/1982 | De Felice | 239/320 |
| 4,470,412 A | 9/1984 | Nowacki et al. | |
| 4,496,086 A | 1/1985 | Duchadeau | |

(Continued)

FOREIGN PATENT DOCUMENTS

EP 0 009 667 4/1980

(Continued)

OTHER PUBLICATIONS

"AARC Clinical Practice Guideline: Use of Positive Airway Pressure Adjuncts to Bronchial Hygiene Therapy." *Respiratory Care*. vol. 38, No. 5. May 1993. pp. 516-520.

(Continued)

*Primary Examiner*—Steven O Douglas
(74) *Attorney, Agent, or Firm*—Merchant & Gould P.C.

(57) ABSTRACT

An apparatus for use in conjunction with a metered dose inhaler which includes a novel valve system to aid in the delivery of aerosolized medicament to a subject. The apparatus also includes a novel rotational flow generator to aid in the useable delivery of said medication and avoid its loss either in the apparatus or by non-useful delivery to said subject.

51 Claims, 6 Drawing Sheets

U.S. PATENT DOCUMENTS

| | | | |
|---|---|---|---|
| 4,509,515 A | 4/1985 | Altounyan et al. | |
| 4,635,631 A | 1/1987 | Izumi | |
| 4,637,528 A | 1/1987 | Wachinski et al. | |
| 4,641,644 A | 2/1987 | Andersson et al. | |
| 4,646,644 A | 3/1987 | Richmond et al. | |
| 4,770,413 A | 9/1988 | Green | |
| 4,796,614 A | 1/1989 | Nowacki et al. | |
| 4,846,168 A | 7/1989 | Abiko et al. | |
| 4,852,561 A | 8/1989 | Sperry | |
| 4,907,583 A | 3/1990 | Wetterlin et al. | |
| 4,940,051 A | 7/1990 | Lankinen | |
| 4,981,295 A | 1/1991 | Belman et al. | |
| 5,012,803 A | 5/1991 | Foley et al. | |
| 5,012,804 A | 5/1991 | Foley et al. | |
| 5,033,463 A | 7/1991 | Cocozza | |
| 5,040,527 A | 8/1991 | Larson et al. | |
| 5,042,467 A * | 8/1991 | Foley | 128/200.23 |
| 5,048,729 A | 9/1991 | Pritchard | |
| 5,109,840 A | 5/1992 | Daleiden | |
| 5,178,138 A | 1/1993 | Walstrom et al. | |
| 5,193,529 A | 3/1993 | Labaere | |
| 5,241,954 A | 9/1993 | Glenn | |
| 5,250,287 A | 10/1993 | Cocozza | |
| 5,280,784 A | 1/1994 | Kohler | |
| 5,297,543 A | 3/1994 | Larson et al. | |
| 5,309,900 A | 5/1994 | Knoch et al. | |
| 5,312,049 A | 5/1994 | Knoch et al. | |
| 5,357,951 A | 10/1994 | Ratner | |
| 5,385,140 A * | 1/1995 | Smith | 128/200.23 |
| 5,427,089 A | 6/1995 | Kraemer | |
| 5,456,249 A | 10/1995 | Kirk | |
| 5,458,136 A | 10/1995 | Jaser et al. | |
| 5,461,695 A | 10/1995 | Knoch | |
| 5,477,849 A | 12/1995 | Fry | |
| 5,479,920 A | 1/1996 | Piper et al. | |
| 5,497,765 A | 3/1996 | Praud et al. | |
| 5,497,872 A | 3/1996 | Pennino | |
| 5,501,214 A | 3/1996 | Sabo | |
| 5,505,194 A | 4/1996 | Adjei et al. | |
| 5,549,102 A | 8/1996 | Lintl et al. | |
| 5,562,093 A | 10/1996 | Gerson | |
| 5,575,282 A | 11/1996 | Knoch et al. | |
| 5,596,982 A | 1/1997 | Blaha-Schnabel | |
| 5,598,839 A | 2/1997 | Niles et al. | |
| 5,617,844 A | 4/1997 | King | |
| 5,629,032 A | 5/1997 | Pennino | |
| 5,645,049 A | 7/1997 | Foley et al. | |
| 5,647,345 A | 7/1997 | Saul | |
| 5,657,853 A | 8/1997 | Pennino | |
| 5,658,221 A | 8/1997 | Hougen | |
| 5,676,130 A | 10/1997 | Gupte et al. | |
| 5,724,959 A | 3/1998 | McAughey et al. | |
| 5,724,962 A | 3/1998 | Vidgren et al. | |
| 5,738,087 A | 4/1998 | King | |
| 5,740,966 A | 4/1998 | Blaha-Schnabel | |
| 5,755,221 A | 5/1998 | Bisgaard | |
| 5,765,553 A | 6/1998 | Richards | |
| 5,775,320 A | 7/1998 | Patton et al. | |
| 5,816,240 A | 10/1998 | Komesaroff | |
| 5,840,279 A | 11/1998 | Narodylo et al. | |
| 5,848,588 A * | 12/1998 | Foley et al. | 128/200.23 |
| 5,881,718 A | 3/1999 | Mortensen et al. | |
| 5,890,998 A | 4/1999 | Hougen | |
| 5,896,857 A | 4/1999 | Hely et al. | |
| 5,899,832 A | 5/1999 | Hougen | |
| 5,925,831 A | 7/1999 | Storsved | |
| 5,957,389 A | 9/1999 | Wunderlich et al. | |
| 6,000,394 A | 12/1999 | Blaha-Schnabel et al. | |
| 6,026,807 A | 2/2000 | Puderbaugh et al. | |
| 6,026,808 A | 2/2000 | Armer et al. | |
| 6,026,809 A * | 2/2000 | Abrams et al. | 128/203.15 |
| 6,039,042 A | 3/2000 | Sladek | |
| 6,044,841 A | 4/2000 | Verdun et al. | |
| 6,085,741 A | 7/2000 | Becker | |
| 6,089,105 A | 7/2000 | Ricciardelli | |
| 6,106,479 A | 8/2000 | Wunderlich et al. | |
| 6,123,075 A | 9/2000 | Kirk | |
| 6,138,673 A | 10/2000 | Shepherd | |
| 6,176,237 B1 | 1/2001 | Wunderlich et al. | |
| 6,228,346 B1 | 5/2001 | Zhang et al. | |
| 6,240,917 B1 | 6/2001 | Andrade | |
| 6,257,231 B1 * | 7/2001 | Shick et al. | 128/200.14 |
| 6,293,279 B1 | 9/2001 | Schmidt et al. | |
| 6,345,617 B1 | 2/2002 | Engelbreth et al. | |
| 6,367,471 B1 | 4/2002 | Genosar et al. | |
| 6,412,481 B1 | 7/2002 | Bienvenu et al. | |
| 6,435,177 B1 | 8/2002 | Schmidt et al. | |
| 6,464,388 B2 | 10/2002 | Ligouzat | |
| 6,481,438 B1 | 11/2002 | Gallem et al. | |
| 6,513,519 B2 | 2/2003 | Gallem | |
| 6,513,727 B1 | 2/2003 | Jaser et al. | |
| 6,514,177 B1 | 2/2003 | Brugger et al. | |
| 6,557,549 B2 | 5/2003 | Schmidt et al. | |
| 6,606,990 B2 | 8/2003 | Stapleton et al. | |
| D483,860 S | 12/2003 | Knoch | |
| 6,679,251 B1 | 1/2004 | Gallem et al. | |
| 6,679,252 B2 * | 1/2004 | Sladek | 128/200.23 |
| 6,848,443 B2 | 2/2005 | Schmidt et al. | |
| 6,962,151 B1 | 11/2005 | Knoch et al. | |
| 6,983,747 B2 | 1/2006 | Gallem et al. | |
| 7,059,320 B2 | 6/2006 | Feiner et al. | |
| 7,077,126 B2 | 7/2006 | Kummer et al. | |
| 7,131,440 B2 | 11/2006 | Sonntag | |
| 2001/0013341 A1 | 8/2001 | Gallem | |
| 2001/0054421 A1 | 12/2001 | Jaser et al. | |
| 2002/0005196 A1 | 1/2002 | Brugger | |
| 2002/0056448 A1 | 5/2002 | Stapleton et al. | |
| 2003/0037785 A1 | 2/2003 | Sonntag | |
| 2003/0037788 A1 | 2/2003 | Gallem et al. | |
| 2004/0089295 A1 | 5/2004 | Gallem et al. | |
| 2004/0094148 A1 | 5/2004 | Lulla et al. | |
| 2004/0250816 A1 | 12/2004 | Kummer et al. | |
| 2005/0056274 A1 | 3/2005 | Kunschir | |
| 2005/0224076 A1 | 10/2005 | Pfichner et al. | |
| 2005/0244339 A1 | 11/2005 | Jauernig et al. | |
| 2006/0048772 A1 | 3/2006 | Borgschulte | |
| 2006/0054166 A1 | 3/2006 | Knoch et al. | |
| 2006/0057073 A1 | 3/2006 | Lintz et al. | |
| 2006/0065267 A1 | 3/2006 | Tran et al. | |
| 2006/0102172 A1 | 5/2006 | Feiner et al. | |
| 2006/0102178 A1 | 5/2006 | Feiner et al. | |
| 2006/0162723 A1 | 7/2006 | Selzer et al. | |
| 2006/0207591 A1 | 9/2006 | Gallem et al. | |
| 2006/0213503 A1 | 9/2006 | Borgschulte et al. | |
| 2006/0254578 A1 | 11/2006 | Boehm et al. | |
| 2006/0289002 A1 | 12/2006 | Hetzer et al. | |

FOREIGN PATENT DOCUMENTS

| | | |
|---|---|---|
| EP | 0 015 247 | 9/1980 |
| EP | 0 134 847 | 3/1985 |
| EP | 0 289 563 | 11/1988 |
| EP | 0 347 779 | 12/1989 |
| EP | 0 372 148 | 6/1990 |
| EP | 0 475 257 | 3/1992 |
| EP | 0 514 085 | 11/1992 |
| EP | 0 678 306 | 10/1995 |
| EP | 0 820 780 | 1/1998 |
| EP | 0 938 908 | 9/1999 |
| EP | 1 358 901 A3 | 12/2003 |
| GB | 975754 | 11/1964 |
| GB | 2 000 555 | 1/1979 |
| GB | 1017032 | 1/1996 |
| GB | 2 299 512 | 10/1996 |

| | | |
|---|---|---|
| JP | 55-40595 | 3/1980 |
| JP | 0 548 152 | 6/1993 |
| WO | WO 91/00117 | 1/1991 |
| WO | WO 92/20391 | 11/1992 |
| WO | WO 96/32149 | 10/1996 |
| WO | WO 97/01365 | 1/1997 |
| WO | WO 98/26827 | 6/1998 |
| WO | WO 99/16490 | 4/1999 |
| WO | WO 00/27455 | 5/2000 |
| WO | WO 00/59565 | 10/2000 |
| WO | WO 01/76671 | 10/2001 |

OTHER PUBLICATIONS

Christensen et al. "Treatment of Bronchial Asthma with Terbutaline Inhaled by Conespacer Combined with Positive Expiratory Pressure Mask." *Chest 100.* vol. 2. Aug. 1991. pp. 317-321.

Hickey et al. "Inhalation Aerosols: Physical and Biological Basis for Therapy." *Marcel Dekker, Inc.* pp. 418-435.

Anderson et al. "A new Mode of Administration Nebulized Bronchodilator in Severe Bronchospasm." *Eur. J. Respir. Dis. Suppl. 119.* vol. 63. 1982. pp. 97-100.

Rau et al. "Combining a Positive Expiratory Pressure Device with a Metered-Dose Inhaler Reservoir System Using Chlorofluorocarbon Albuterol and Hydrofluoroalkane Albuterol: Effect on Does and Particle Size Distributions." *Respiratory Care.* vol. 45. No. 3. 2000. pp. 320-326.

Rau. Respiratory Care Pharmacology $4^{th}$ Edition. 1994. Mosby. pp. 256-261.

Meeran et al. "Oral and Inhaled Corticosteroids Reduce Bone Formation as Shown by Plasma Osteocalcin Levels." *Am. J. Respir. Crit. Care. Med.* vol. 151. 1995. pp. 333-336.

Merriam-Webster's Collegiate Dictionary, Tenth Ed. ISBN 0-87779-707-2. 1993. p. 86.

Mahlmeister et al. "Positive-Expiratory-Pressure Mask Therapy: Theoretical and Practical Considerations and a Review of the Literature." *Respiratory Care.* vol. 36. No. 11. 1991. pp. 1218-1229.

Newman. "Aerosol Deposition Considerations in Inhalation Therapy." *Chest.* vol. 8. No. 2. 1985. pp. 152-160.

Contents. "Technology Showcase: Adjuncts to Bronchial Hygiene Therapy." *AARC TImes.* 1998. pp. 12-14.

Ventlab Corporation. "Ventlab BreatheRite." http://www.ventlab.com/mdi.htm. 2000.

Pamphlet for "PARI PEP System. Part No. 18F61." 2001. pp. 1-4.

Pamphlet for "TheraPEP: Positive Expiratory Pressure Therapy System." No. 20-112. 2001. pp. 1-5.

photographs for Ventlab BreatheRite holding chamber. 3 pages.

Callahan. "K981944-BreatheRite." Letter from Dept. of Health & Human Services with enclosures. 1998. pp. 1-3.

Office Action mailed Mar. 5, 2009 for U.S. Appl. No. 11/655,039 - Schmidt.

* cited by examiner

AEROSOL MEDICATION INHALATION SYSTEM

This application is a continuation of U.S. patent application Ser. No. 10/137,007 filed May 2, 2002, now abandoned.

BACKGROUND

The present invention is directed to apparatus for delivering aerosol medicament to a subject in need of the medicament. Delivery systems start with an aerosol-generating device. One common example of such devices is a pressurized metered dose inhaler (MDI). MDIs use pressurized gases to disperse medicament as tiny particles or droplets for delivery to the subject. By depressing the MDI, a known quantity of gas, and thereby of medicament, is ejected from the MDI. MDIs have been used with various types of diverse apparatus, in attempts to improve the delivery of this known quantity of medicament to the subject. Some problems associated with the delivery of medicament in an aerosol form include, but are not limited to, wastage of medicament in the delivery apparatus, delivery at too high speeds so that medicament sticks to the back of the subject's throat or is inhaled into the subject's sinuses rather than being received into the lungs, ejection of medicament out of the apparatus towards a subject without inhalation thereby, and ejection of medicament from the MDI upon exhalation by the subject into the apparatus prior to inhalation.

SUMMARY OF THE INVENTION

In one aspect, the present invention provides a mouthpiece with a valve for controlling the delivery of aerosolized medicament to a subject. The mouthpiece includes a housing that defines a passage through which the medicament flows to the subject. The housing has a one-piece valve system that permits passage of medicament aerosol to the subject during inhalation, but does not permit the passage of the subject's breath in the upstream direction during exhalation, with the exhaled breath being expelled through an opening in the sidewall of the housing.

Another aspect of the present invention combines this mouthpiece and valve system with a holding chamber, which is disposed between the mouthpiece and the source of aerosol. In a further feature of this aspect of the invention, the interior of the holding chamber has anti-electrostatic properties to reduce the amount of medicament adhering to the walls of the holding chamber and thereby increase the delivery efficiency of the system.

In a further aspect of the present invention, a holding chamber is provided with a receptacle member adapted to accept a source of aerosol medicament. The receptacle member may aid in the efficient delivery of medicament to the subject, for example by being vented to allow outside air to be mixed with the medicament aerosol in the holding chamber. In addition, if a rotation is imparted to the outside air brought into the holding chamber, the adhesion of medicament to the walls of the holding chamber can be reduced and the effort necessary to inhale through an apparatus of this type may be reduced.

DETAILED DESCRIPTION

Figure 1:
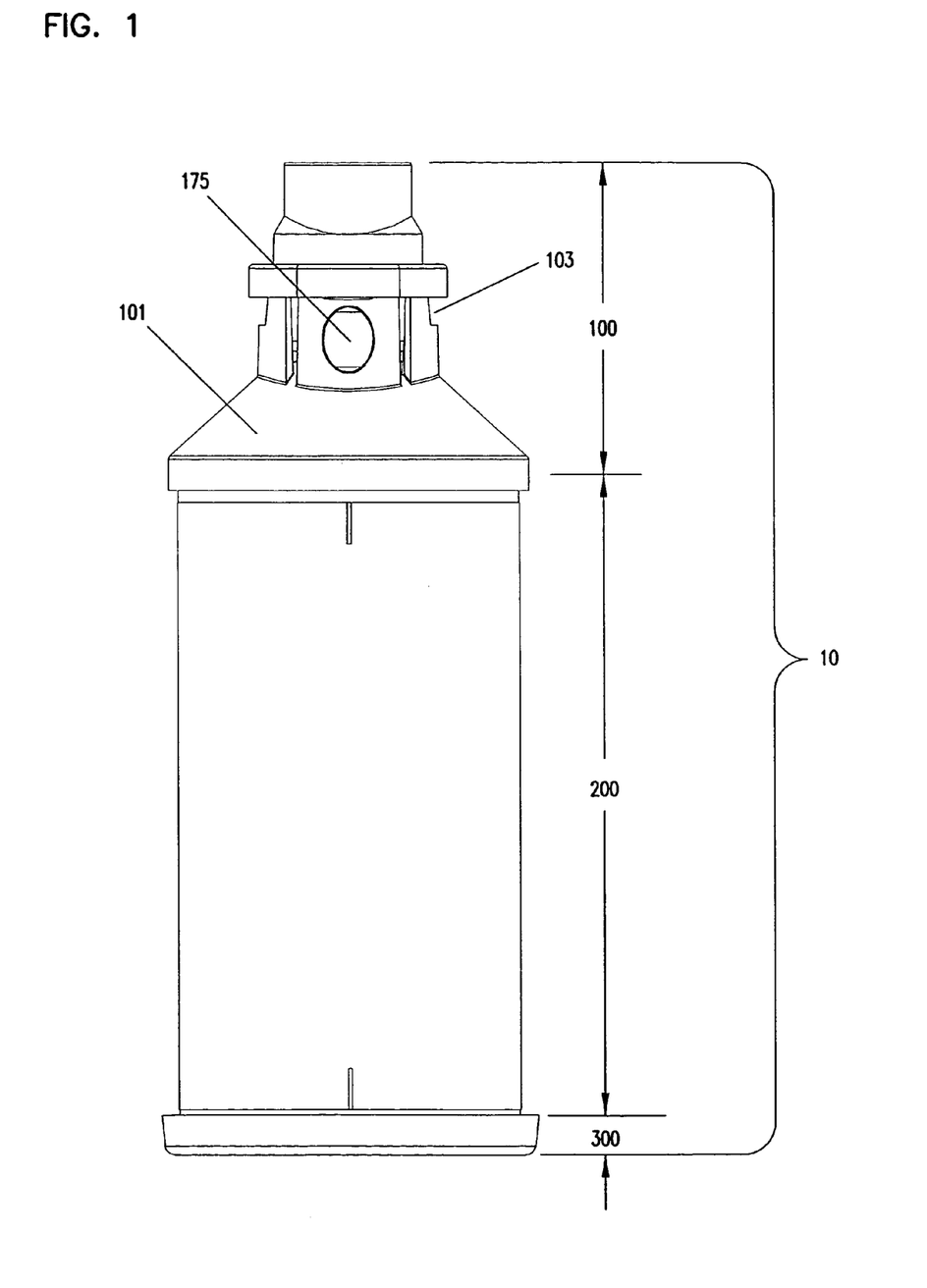
FIG. 1 is an assembled view of an example of the aerosol medicament delivery apparatus of the present invention.
Figure 2:
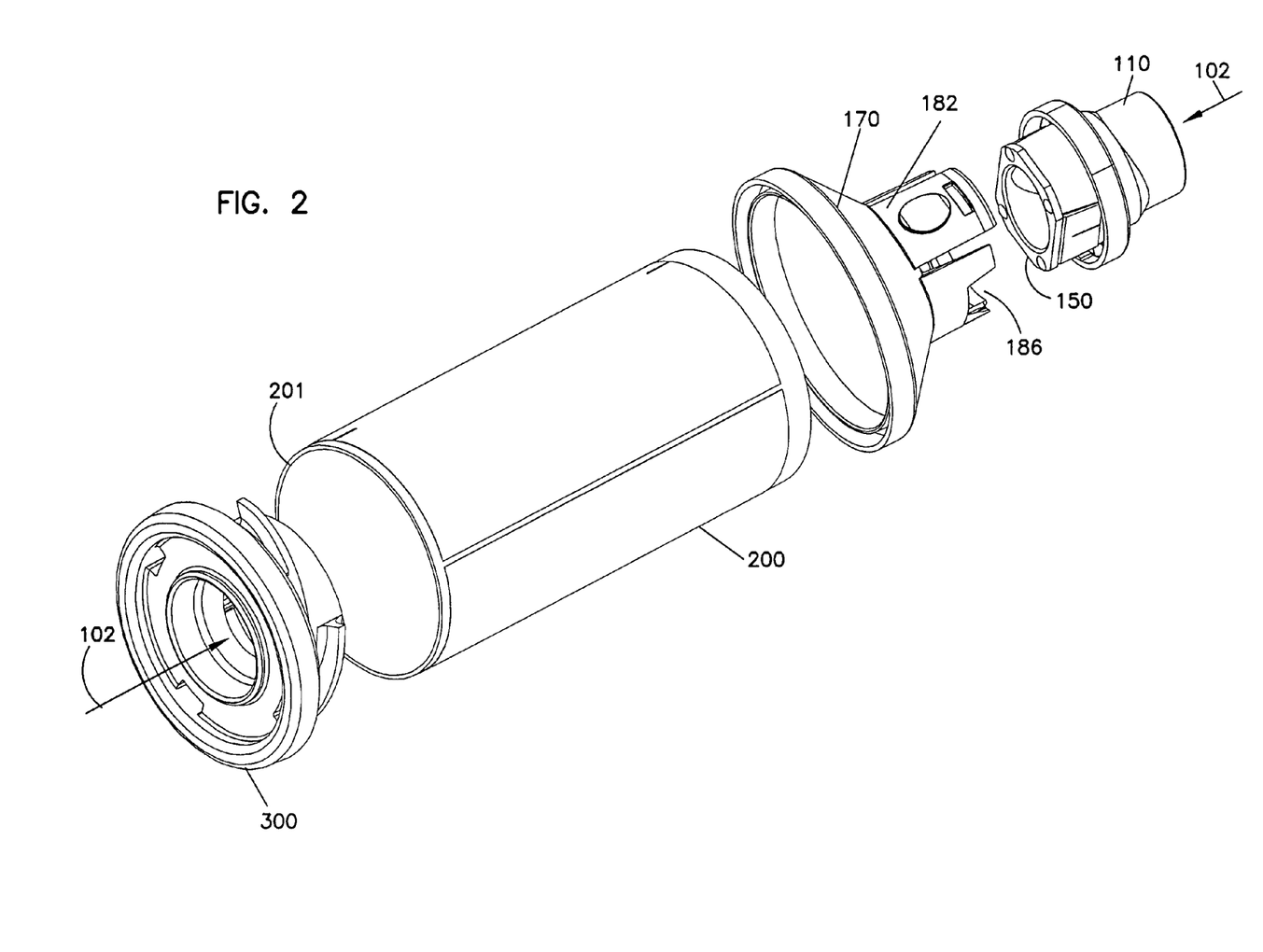
FIG. 2 is a perspective exploded view of the apparatus.

Referring to FIGS. 1 and 2, the aerosol medicament delivery apparatus 10 of the present invention is composed of a holding chamber 200 with first and second ends. At the first end of the holding chamber is a receptacle 300 for connection to a source of aerosol medication. For the purposes of the present invention, aerosol medicament or aerosol medication is intended to include finely divided solid or liquid materials that are carried by a gas for delivery to a subject's respiratory tract, especially to the lungs. This includes nebulized materials. The medicament and carrier gas aerosol composition can be prepared prior to use if it exhibits sufficient physical and chemical stability, or it can be prepared in situ from sources of solid or liquid medicament materials (either in pure form or combined with a suitable solid or liquid solvent, excipient or diluent) and pressurized gas.

At the second end is a mouthpiece member 100 for delivering aerosol medicament to a subject through a valve 150. The mouthpiece member includes a housing 101 that defines a passage 102 through which aerosol medicament can be supplied to a subject and has an opening 103 that opens to the outside of the housing. The valve, discussed below, is of one-piece construction. During inhalation the valve permits the flow of aerosol medicament from the holding chamber to the subject, while blocking the inflow of outside air to the passage 102 through the sidewall of the housing of the mouthpiece member. During exhalation, the valve blocks the flow of exhaled air upstream in the direction of the holding chamber, and permits the exhaled air to be exhausted through the sidewall of the housing.

In an exemplary embodiment, the housing 101 is composed of a delivery member 110 and an adaptor member 170. The opening 103 may be defined, as it is in part in the exemplary embodiment, by a notch 186 in the adaptor member. The delivery member and adaptor member may be releasably connected by a quick release mechanism 182. In the exemplary embodiment, the quick release mechanism is a flexible wall, upon which a positioning element 175 may be located. Also, in the exemplary embodiment, the housing is transparent. This has the advantage that it allows for the subject to visually verify the operation of the valve, to ensure opening and closing during treatment.

Figure 3:
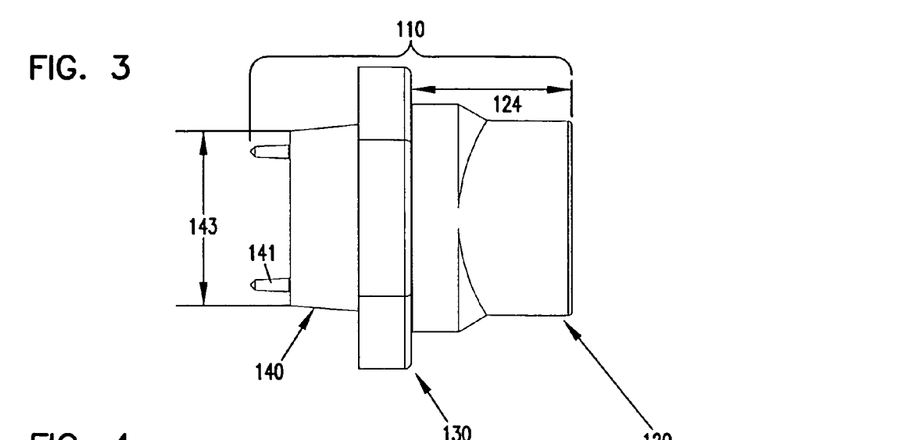
FIG. 3 is a side view of the delivery member used in the apparatus.

Referring to FIG. 3, the delivery member 110 may include a subject side section 120, a connecting ring 130, and an adaptor side section 140. In the exemplary embodiment, the subject side section of the delivery member of the mouthpiece is sized and shaped to fit a human mouth, e.g. having an oval shape. The subject end section is defined by a housing composed of a sidewall having a height 124, and upon which may be provided at least one ridge 125. Positioning pins 141 may be provided on the adaptor side section of the delivery member.

Figure 4:
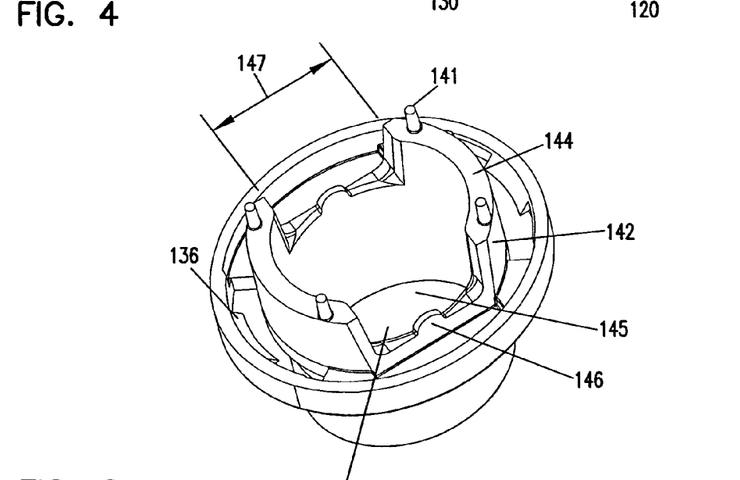
FIG. 4 is a bottom perspective view of the delivery member.

Referring to FIG. 4, the adaptor side section 140 of the delivery member 110 in this exemplary embodiment has walls 142 arranged around an opening 145. One or more openings, for example the illustrated notches 147, is formed in the wall 142 and can define an exhaust opening from the delivery member for exhaled air. This opening is closed by the valve during inhalation, and the opening may be provided with an element to assist in seating a valve member, for example protrusion 146. The end face 144 of the wall can be used as a surface for holding the valve in place when the apparatus is assembled, in cooperation with an opposed surface on the adaptor member. Also, in this embodiment, the four positioning pins 141 extend from the end face of the wall 142.

Figure 5A:
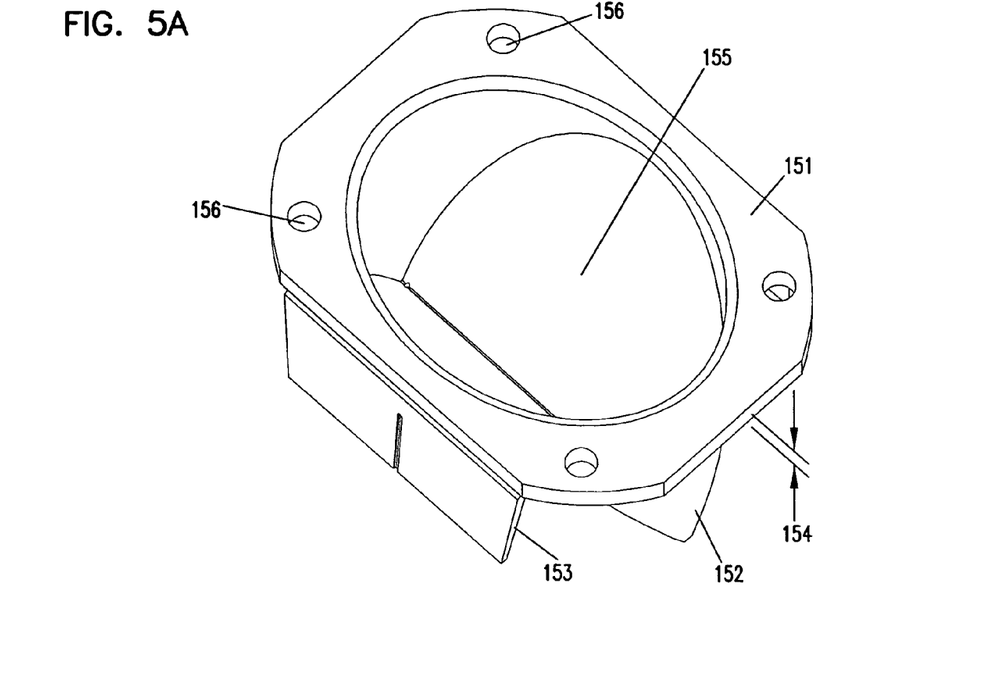
FIGS. 5a and 5b are top and bottom views of the valve element used in the apparatus.
Figure 5B:
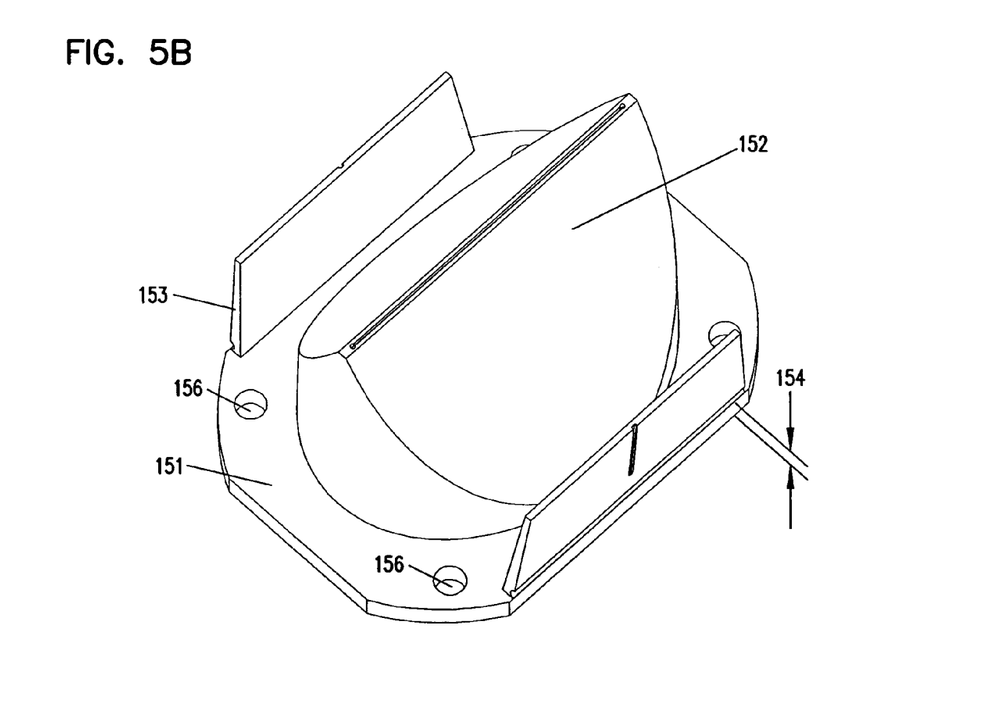

Referring to FIGS. 5a and 5b, the one-piece two-way valve system 150 allows for inhalation and exhalation with a single valve. The valve has a base 151, a first valve element 152, which has a duck-bill shape in this embodiment, and a second valve element 153, which is shaped like a hinged flap 153 in this embodiment. In the exemplary embodiment, the valve is composed of a flexible material and there are two hinged flaps 153. The two valve elements may be joined at or carried on a common base 151. The base has a thickness 154 that is less than the height of the positioning pins of the mouthpiece, so that the pins may pass therethrough. There is an opening 155 in the base, which may be defined as the perimeter of contact between the duck-bill and the base. The exemplary embodiment has four positioning holes 156 placed near the perimeter of the base, each being sized to admit the matching positioning pins. Thus, when the apparatus is assembled, the positioning pins of the mouthpiece penetrate the positioning holes of the valve base and the valve base forms a substantially airtight seal between the delivery member and the adaptor member.

The duck-bill is a shape predominantly that of a wedge with a very narrow split across the apex of the wedge. The split is narrow enough that the two edges forming the ends of the duck-bill are substantially in contact when there is no external pressure on the duck-bill. The duck-bill has a span, a height, and a thickness. The height of the duck-bill is the vertical distance between the apex of the wedge where the split is located and the base. The span is the distance of the split across the thin edge of the wedge and the height. The span is sufficiently narrow that the apex of the duck bill will fit within the delivery member without contacting it. Thus, the dead zone within the delivery member is minimized by the valve extending therein. The valve may be as wide as possible to provide for easier inhalation, but just narrower than the passage so that the duck-bill sides do not receive pressure and the lips of the duck-bill are not parted except by inhalation.

Dead space refers to the volume of the apparatus containing air which is rebreathed. Dead space is inherent in any valve-based system enclosed within a mouthpiece or mask; it is the space between the mouth of a subject and the valve. Any subject has a limited volume of air that may be inhaled, and which then is exhaled. This is the subject's tidal volume. The inhalation air will contain both oxygen and medicament. The exhalation air will contain carbon dioxide. In a sealed system, all inhalation air will come through the valve and will contain a preferable mixture of medicament laden air. However, this inhalation air will be combined with whatever gases remain sealed within the dead space on their way to being actually inhaled into the subject's respiratory tract. Similarly, when the subject exhales, all air must pass through this dead zone on the way out the exhaust portion of the valve system.

Because the subject will be incapable of forcing a complete vacuum within this sealed system, the dead space will contain gases that then will be re-inhaled during the next breathing cycle. Given that the volume of the subject's lungs is fixed, the larger the volume of the system's dead space, the smaller the volume of medicament laden air the subject will receive with each breathing cycle. Thus, the larger the volume of dead space, the less efficient the system because increasing dead space causes a buildup of carbon dioxide and rebreathing. Rebreathing carbon dioxide can have an adverse effect on breathing rates and patterns, especially for small children who have very small tidal volumes. Duck-bill valves are more efficient than diaphragm valves because the volume encompassed by the duck-bill is subtracted from space that otherwise would be dead space in a diaphragm-based system.

The duck-bill is thin enough that the sides of the wedge will flex when the atmospheric pressure on the opposite side of the base from the duck-bill is greater than that above the duckbill. This causes the edges of the duck-bill to part, letting air flow through the duck-bill in the direction from the base to mouthpiece. Thus, in the present embodiment, air is permitted to flow through the mouthpiece to a subject during inhalation. The duck-bill closes automatically at the end of inhalation when the atmospheric pressure differential is removed. Thus, the flow of exhaled air upstream of the valve to the holding chamber is prevented during exhalation.

The exemplary embodiment of the present invention provides two hinged flaps 153 extending from on or near the perimeter of the base. Each hinged flap 153 is sized so as to be able to cover a corresponding notch 147 when assembled. Each flap is placed on the base at such a position and at such an angle that when the base is placed onto the positioning pins of the mouthpiece, the flap covers one of the notches 147. The flag is hinged on the base so that it may cover the notch 147 during inhalation, thereby preventing the flow of outside air into the interior of the housing through the opening in the sidewall of the housing. When the mouthpiece of the apparatus of the exemplary embodiment is assembled, the notch of the delivery member 147 and the aforementioned notch of the adaptor member 186 may be aligned radially, and the hinged outgas flap 153 is disposed between these notches. The flexible material forming each of the outgas flaps is sufficiently thin to allow an outgas flap to flex through at least a few degrees of flexibility when differences in relative atmospheric pressure caused by human breathing exert flexing pressure on said flap, thereby moving the flap away from the notch 147 during exhalation and allowing exhaled air to pass out of the mouthpiece through the notch 186.

Figure 6:
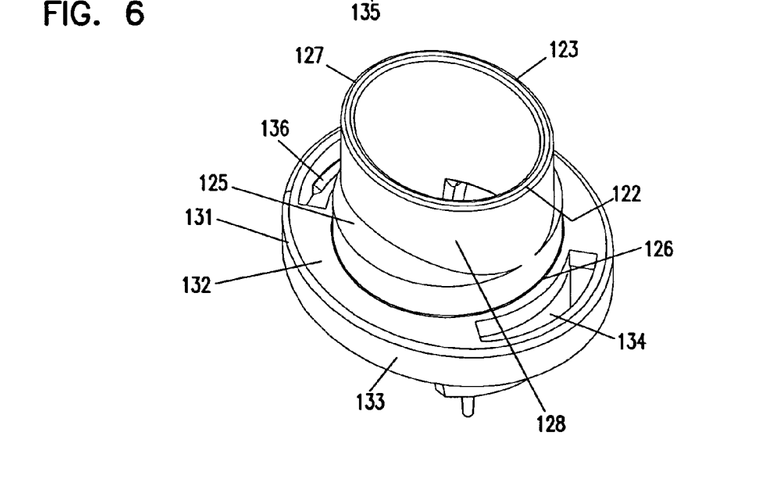
FIG. 6 is a top perspective view of the delivery member.

Referring to FIG. 6, the subject side section 120 of the delivery member may be formed by a sidewall 128 that is generally cylindrical in shape with an oval cross section. The exemplary embodiment has two side points 122, opposite each other on the sidewall, and two lip points 123, opposite each other on the sidewall. Each lip point is equidistant between the two side points. There is a contact end 126 where the sidewall is joined to the connecting ring and a lip end 127 opposite the contact end. The upper opening of the sidewall 121 at the lip end is oval. There is a lower opening of the sidewall at the contact end, through which the tip of the duck-bill valve passes.

Ridges 125 may be provided for placement of the subject's lips, or to aid in the placement of an adaptor mask on the outside of the delivery member. Shaped correctly, a ridge 125 may be used to seal and mount such a mask with a tight pressure fit. These ridges are placed approximately halfway down the upper section, and are wedge shaped in the exemplary embodiment. Specifically, they are formed by the upper and lower thickness measurements being equal at the side points and the lower thickness being greater than the upper thickness at the lip points.

Referring to FIGS. 4 and 6, the connecting ring 130 between the adaptor side and subject side sections of the delivery member has an interior opening 135, which may be equal in size to and substantially continuous with the opening of the sidewall of the subject side section. It has an exterior limit 131 that is greater than the interior opening, and a surface 132 where the connecting ring is joined to the subject side section. The surface 132 extends from the sidewall 128 outwards toward the exterior limit 131 where it joins with an exterior wall 133.

The exterior wall 133 may be substantially parallel to the sidewall 128 and extends from the top surface in a direction away from the lip end of the subject side section. The exterior wall has an interior surface and an exterior surface, the interior surface being closer to the interior opening of the connecting ring. In the exemplary embodiment, there are two contact openings 134 in the top surface, which are disposed approximately equidistantly around the circumference of the top surface. Each contact hole is adapted to accept a portion of the adaptor member, to help hold the two members of the mouthpiece securely together. On the interior surface of the exterior wall, there may be provided two engaging members 136, or catches, each being below a contact hole. They are wedge shaped and oriented with the thin end of the wedge towards the adaptor side for ease in connecting and resistance to disconnecting. In the exemplary embodiment, each has a width less than that of the corresponding contact opening above the catch, a length less than that of the distance between the top and bottom of the exterior wall of the connecting ring, and a height less than the length.

Referring back to FIGS. 3 and 4, the width 143 of each section that makes up the wall 142 is approximately as wide as a contact opening in the top surface of the connecting ring. Each wall section is disposed along the interior opening substantially adjacent to a contact opening, thus providing a limit to the flexing of the walls of the adaptor member, which is discussed below. In the exemplary embodiment, each wall section has two positioning pins 141 placed along the end face of the wall, extending in the same direction. They are placed near the edge of the wall sections, and can be placed as far apart from each other as the width of a contact opening in the surface of the connecting ring. Due to their height, the sections of the wall 142 extend into the space of the adaptor member when the apparatus is assembled. Protrusions 146 may be disposed on the perimeter of the opening forming the passage for exhalation air flow (notches 147). These protrusions act as stop elements for the exhaust flap portions of the one-piece valve, limiting their travel in an inward direction. As will be seen in more detail below, when the subject inhales, these exhaust flaps are pressed by suction against the stop elements and form a seal so that the pressure of inhalation is fully directed towards drawing the medicament laden air from the holding chamber.

Figure 7:
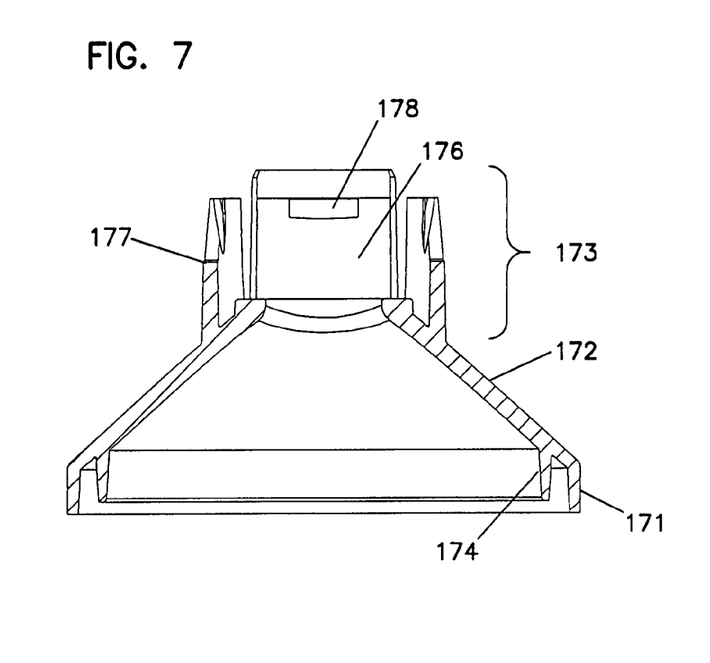
FIG. 7 is a sectional side view of the adapter member used in the apparatus.

Referring to FIG. 7, the adaptor member 170 may be generally frustoconical in shape, thereby providing for the smooth change in diameter from the holding chamber to the delivery member. In the exemplary embodiment, it is both frustoconical and transparent. A transparent embodiment of the present invention has the additional advantage of allowing the subject to visually verify the presence of the medicament during delivery to the patient. The adaptor member may have a base end 171, a conical midsection 172, four wall sections, and a delivery side end 173. The base end is adapted to cooperate with the edge of the holding chamber, for example forming an exterior wall extending from the end of the cone. The base end of the adaptor member also may have an inner wall 174 extending from the end of the cone. In the exemplary embodiment, each of these two walls having a height of at least 0.5 mm to define a groove for accepting the edge of the holding chamber. In this case, the walls are shaped and positioned such that, when the chamber is positioned between the inner and outer walls and a thin layer of adhesive is applied between the walls, a substantially airtight seal may be formed between the holder and the chamber. Other systems for joining the adaptor member and holding chamber may be used, including permanent bonding or releasable connections. The releasable connection may not be needed when the delivery member is made of two readily-separated components that allow for easy cleaning and for replacement of the valve when necessary, as in the illustrated embodiment.

Figure 8:
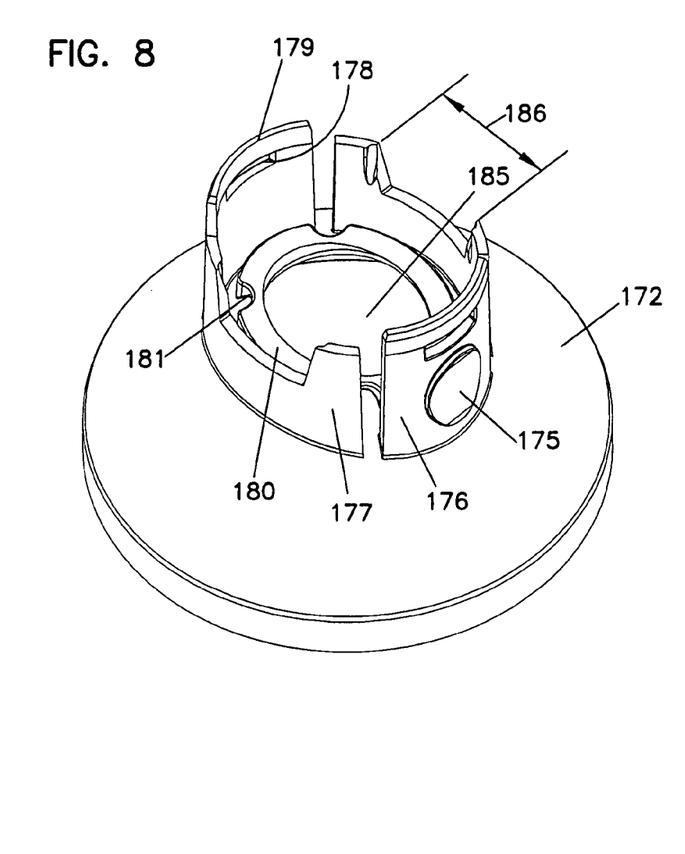
FIG. 8 is a top perspective view of the adaptor member.

Referring to FIGS. 7 and 8, the wall arising from the frustoconical midsection 172 of the adaptor member 170 may be divided into four sections, including two catch walls 176 and two vent walls 177 in the exemplary embodiment. These may be placed alternately around the delivery side end of the adaptor member. Each catch wall 176 may have a catch opening 178 sized to admit one of the catches 136 of the connecting ring 130 of the delivery member 110. A catch wall 176 is positioned on the adaptor member such that its opening 178 is adapted to fit a catch 136 when the two adaptor and delivery members are joined. The end 179 of the catch wall 176 may fit a contact opening 134 of the connecting ring 130 of the delivery member 110. The catch walls 176 may be flexible, so that they may be bent by the subject applying pressure at the positioning points 175 to release the catch 136 from the opening 178. This allows the two members of the exemplary housing 101 to be joined and separated in a quick-release fashion. Each valve wall 177 in the exemplary embodiment is U shaped. That is, it is a wall on the long side of the oval opening with a notch 186 in it. Other systems for connecting the adaptor member and delivery member can be used. In addition, the catch and opening could be reversed, i.e. the opening provided on the connecting ring and the catch provided on wall section of the adaptor member.

The delivery side end of the conical adaptor member may have an opening 185 of substantially the same size as the opening 155. An airtight seal may be formed between the opposing surfaces of the adaptor member and the delivery member by the valve. That is, the valve base 151 may have opposing surfaces arranged to meet those of the adaptor member and the delivery member and form an airtight seal when the apparatus is assembled. The exemplary embodiment's adaptor member 170 has a rim 180 around the opening 185 with four positioning openings 181 in the rim, one for each pin 141. Thus, when the two members are joined, the four pins of the delivery member drop into these openings in the exemplary embodiment.

Referring to back FIGS. 1, 2 and 7, the cylindrical holding chamber 200 may be defined by a length of cylindrical tube that extends between the mouthpiece 100 and a source of aerosol medicament and includes the receptacle 300 accepting an outlet from a source of aerosol medicament such as a metered dose inhaler or the like. The tube wall 201 may be sized to fit between the inner wall 174 and the outer wall 171 of the base of the mouthpiece. In the exemplary embodiment, the holding chamber is made of a lightweight metal or alloy, such as aluminum or an alloy thereof.

The use of such material reduces the risk of resistance to medicament flow by static attraction between the particles of medicament and the holding chamber wall. Alternatively, the surface of a holding chamber of any material may be treated with an anti-electrostatic coating or process to achieve this advantage. In the exemplary embodiment using a metal tube, the tube is anodized which provides the advantage of sealing the micro-porosity of such a tube's surface and stabilizing it against oxidation.

Figure 9A:
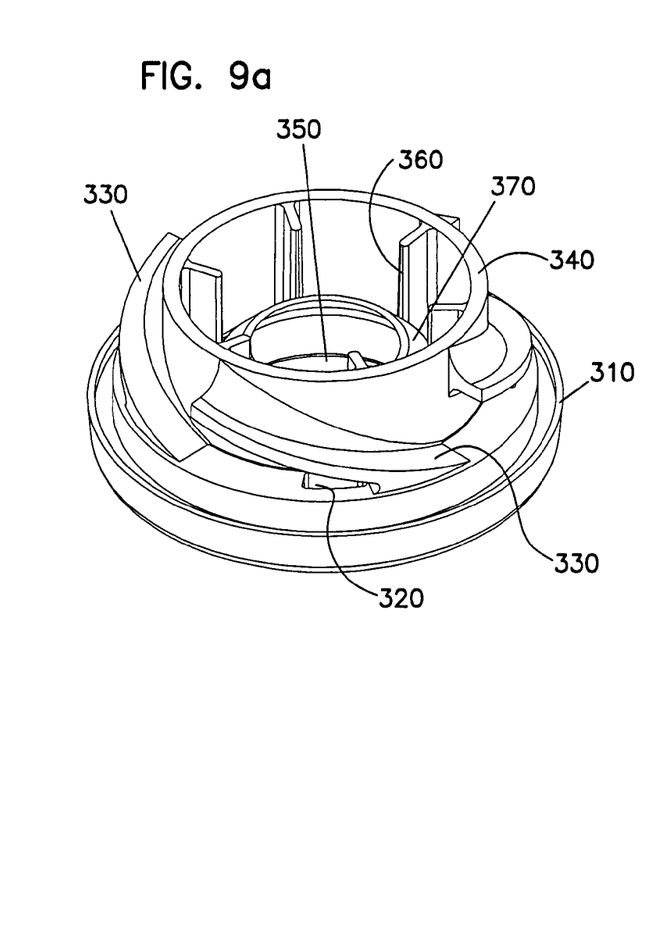
FIGS 9a and 9b are top and bottom views of the receptacle member used in the apparatus.
Figure 9B:
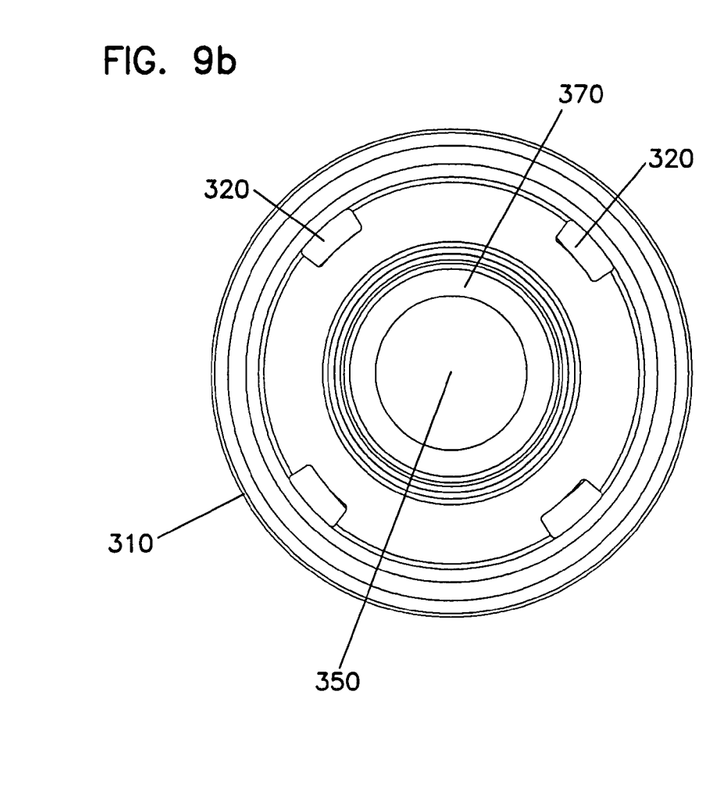

Referring to FIGS. 9*a* and 9*b*, the receptacle 300 may include a base with a lip 310, an opening 350 for accepting a source of aerosol medicament in the base with a collar 370 extending into the chamber 200, an air vent 320, and a supporting wall 340 that surrounds the opening arising from the base into the chamber. The exemplary embodiment has four vents. The receptacle base is sized to fit within the tube of the holding chamber. It may be formed of a resilient and flexible material such that it may be removed from the chamber tube (e.g., for cleaning) and replaced many times without loss of functionality, such as maintenance of structural integrity or the ability of the receptacle to form a substantially airtight seal with the tube, throughout the life of the apparatus. In the exemplary embodiment, the receptacle may be removed and replaced hundreds of times without ripping, tearing or otherwise harming the functionality of the apparatus. This removal resilience also applies to the removal and replacement of the source of aerosol medicament from the apparatus. The lip 310 of the receptacle fits around the perimeter of the base of the member so that the lip extends beyond the edge of the tube. The lip may be sized such that it forms a substantially airtight seal with the tube. Other systems can be used to join the receptacle to the tube if desired.

The opening 350 of the receptacle of the exemplary embodiment may be sized to accept several different types of aerosol medicament sources such as MDIs. The collar 370 is sufficiently long and flexible to form a seal with an aerosol medicament source when one is admitted into the receptacle. The supporting wall 340 of the exemplary embodiment is provided with cyclone baffles 330 placed upon the outside of the wall (relative to the opening) and support ribs 360 radially placed upon the inside of the wall. The support ribs 360 extend from the wall towards the collar 370. They are sized so that there is space for the collar to be pressed up against the ribs when a typical MDI is inserted into the opening. Thus, an airtight seal may be formed around the source of the aerosol medicament. The support ribs of the exemplary embodiment provide support to the source of aerosol medicament by holding that source against the structure of the collar.

The vents 320 allow outside air to be drawn into the holding chamber during inhalation. This helps to push the aerosol medicament to the subject during inhalation. Each cyclone baffle 330 extends towards the base and is aligned with a vent 320 so that the point where the baffle reaches the base is just beyond the vent. The baffle thus covers the vent. The baffle may have a width sufficient to form a seal between the supporting wall and the tube wall of the chamber. By using the baffle to direct airflow coming through the vents, a rotational flow is imparted to the air entering the chamber through the vents. In the exemplary embodiment, the placement of the cyclone baffles above the vents and next to the wall of the holding chamber wall directs outside air to and along the wall of the holding chamber. This reduces the tendency for medicament to adhere to the wall of the holding chamber. Although each of the four vents have been provided with a cyclone baffle in the present embodiment, this may not be necessary in all cases.

The exemplary embodiment of the present invention is steam autoclavable either assembled or disassembled. This advantage arises from both the choice of materials used, as herein discussed, and the materials and methods of assembling the components of the invention, such as the quick release mechanism 182 and the use of high-temperature adhesive at the junction of adaptor member 170 and holding chamber 200. Further, the present invention is easily disassembled for cleaning and parts replacement by a non-technical person.

While a detailed description of the present invention has been provided above, the invention is not limited thereto. Modifications that do not depart from the scope and spirit of the invention will be apparent to those skilled in the art. The invention is defined by the claims that follow.

What is claimed is:

1. An apparatus for aerosol medication delivery, comprising:

a holding chamber having a first and second ends, the first end being adapted to accept a source of aerosol medicament; and a mouthpiece member provided at the second end of the holding chamber, for delivering aerosol medicament to a subject, the mouthpiece member comprising:

a housing defining a passage through which aerosol medicament can be supplied to a subject and comprising a sidewall in which an opening is formed that opens to the outside of the housing; and a one-piece valve member comprising a first valve element in fluid communication with the mouthpiece and the holding chamber, the first valve element within the passage to permit delivery of aerosol to a subject during inhalation and blocks the passage during exhalation and a second valve element in fluid communication with the mouthpiece and the opening in the side wall, the second valve element to prevent air from reaching the subject through the opening in the sidewall of the housing during inhalation and permits the flow of air to the outside of the housing from the passage during exhalation, wherein the first valve element extends axially away from the housing when the apparatus is in a rest position.

2. The apparatus of claim 1, wherein the housing defining the passage comprises a delivery member and an adaptor member, the adaptor member is provided at the second end of the holding chamber, and the delivery member is releasably connected to the adaptor member.

3. The apparatus of claim 2, wherein the opening in the sidewall of the mouthpiece member is provided in the adaptor member.

4. The apparatus of claim 2, wherein the opening in the sidewall of the mouthpiece member is provided in the delivery member.

5. The apparatus of claim 2, wherein the opening in the sidewall is defined by a notch defined in an edge of the adaptor member and a notch defined in an edge of the delivery member.

6. The apparatus of claim 2, wherein the delivery member is releasably connected to the adaptor member by a quick-release mechanism.

7. The apparatus of claim 6, wherein the quick-release mechanism comprises a flexible wall disposed on one of the adaptor member or the delivery member, the flexible wall comprising an engaging member that releasably engages the other of the adaptor member or the delivery member.

8. The apparatus of claim 7, wherein the flexible wall comprises a positioning element adapted for a human digit, placed to define a location for flexing the wall to release the engaging member.

9. The apparatus of claim 1, wherein the mouthpiece is sized and shaped to fit a human mouth.

10. The apparatus of claim 1, wherein the delivery member is provided with a ridge.

11. The apparatus of claim 10, wherein the ridge is adapted for attaching a mask.

12. The apparatus of claim 1, wherein the housing has a stop element that limits the range of motion of the second valve element in the direction of the passage.

13. The apparatus of claim 12, wherein the stop element is disposed on the delivery member.

14. The apparatus of claim 1, wherein the first valve element is a duck-bill valve.

15. The apparatus of claim 1, wherein the member is composed of a flexible material.

16. The apparatus of claim 1, wherein the second valve element is a hinged flap that seats adjacent the opening in the sidewall.

17. The apparatus of claim 2, wherein the first valve element and the second valve element are joined together at a valve base.

18. The apparatus of claim 17, wherein the valve base forms a substantially airtight seal between the delivery member and the adaptor member.

19. The apparatus of claim 2, wherein the adaptor member and the delivery member define first and second opposed surfaces and the valve member is held between the first and second opposed surfaces.

20. The apparatus of claim 19, wherein one of the delivery member and the adaptor member comprises a plurality of pins that extend from one of the first and second opposed surfaces and the other of the delivery member and the adaptor member comprises openings for accepting the pins.

21. The apparatus of claim 20, wherein the valve member is provided with openings through which the pins extend.

22. The apparatus of claim 5, wherein the notch of the delivery member and the notch of the adaptor member are aligned radially when the mouthpiece is assembled.

23. The apparatus of claim 22, wherein the second valve element is disposed between the notches.

24. The apparatus of claim 2, wherein one of the delivery member or the adaptor member comprises a pair of radially spaced walls and the other of the delivery member or the adaptor member comprises a wall that extends into the space between the spaced walls.

25. The apparatus of claim 1, wherein the mouthpiece member has a first end adapted to the second end of the holding chamber and a second end for delivery of the aerosol medicament, which has an oval shape in lateral cross section.

26. The apparatus of claim 1, wherein the housing of the mouthpiece member has inner and outer walls disposed at and in contact with the holding chamber such that the second end of the holding chamber extends into a space between the inner and outer walls.

27. The apparatus of claim 1, wherein the mouthpiece member is connected to the holding chamber by an adhesive.

28. The apparatus of claim 1, wherein the mouthpiece is formed of a transparent material.

29. The apparatus of claim 1, wherein the housing is formed from a transparent material.

30. The apparatus of claim 2, wherein the adaptor member is substantially frustoconical in shape.

31. The apparatus of claim 2, wherein the adaptor member is formed from a transparent material.

32. The apparatus of claim 2, wherein the delivery member is formed from a transparent material.

33. The apparatus of claim 1, wherein the holding chamber is cylindrical.

34. The apparatus of claim 33, wherein the holding chamber is formed of metal.

35. The apparatus of claim 1, wherein the holding chamber is treated with an anti-electrostatic coating.

36. The apparatus of claim 1, further comprising a receptacle member at the first end of the holding chamber, having an opening adapted to receive an outlet of an aerosol generating device.

37. The apparatus of claim 36, wherein the opening in the receptacle member is capable of accepting outlets of different aerosol generating devices.

38. A mouthpiece member for aerosol medicament delivery, having first and second ends, the first end being adapted to accept a source of aerosol medicament and the second end being adapted for delivering aerosol medicament to a subject, the mouthpiece member comprising:
a housing defining a passage through which aerosol medicament can be supplied to a subject and comprising a sidewall in which an opening is formed; and
a one-piece valve member comprising a first valve element that permits delivery of aerosol to a subject during inhalation and blocks the passage during exhalation and a second valve element that blocks the opening in the sidewall of the housing during inhalation and permits the flow of air to the outside of the housing from the passage during exhalation, wherein the first valve element extends axially away from the housing in a rest position.

39. The mouthpiece of claim 38, wherein the housing comprises a substantially frustoconical section.

40. An apparatus for aerosol medication delivery, comprising:
a mouthpiece member for delivering aerosol medicament to a subject,
a holding chamber having first and second ends, the mouthpiece member being disposed at the second end of the chamber and
a receptacle member being disposed at the first end of the chamber, the receptacle member comprising:
an opening adapted to accept a source of aerosol medicament,
a vent permitting fluid communication for the entry of outside air into the holding chamber, and
a means for imparting a rotational flow to the outside air entering the holding chamber,
wherein at least a portion of the means for imparting rotation flow is spaced from the vent and at least partially obscuring the vent when the receptacle member is viewed from above.

41. The apparatus of claim 40, wherein the opening of the receptacle creates an airtight seal around the source of aerosol medicament.

42. The apparatus of claim 40, wherein the receptacle member is formed of a flexible material such that the receptacle member may be removed from and replaced on the holding chamber without loss of functionality.

43. The apparatus of claim 40, wherein the receptacle member has a plurality of vents, disposed equidistantly around the receptacle member.

44. The apparatus of claim 40, wherein the receptacle member directs outside air to the wall of the interior of the holding chamber, thus creating a flow of such air along the wall of the holding chamber and reducing particulate deposit from the aerosol medicament within the holding chamber.

45. The apparatus of claim 40, wherein the means to impart rotational flow comprises at least one baffle disposed on the receptacle member to direct air entering the holding chamber through a vent into a rotational flow within the chamber.

46. The apparatus of claim 42, wherein the receptacle member has a lip around the perimeter of the receptacle member, which enclosed the first end of the holding chamber.

47. The apparatus of claim 40, wherein the receptacle member comprises support ribs for supporting the source of aerosol medicament.

48. The apparatus of claim 47, wherein the opening of the receptacle member is defined by a collar that extends inward and may be pushed up against the support ribs for retaining the source of aerosol medicament.

49. The apparatus of claim 48, wherein the support ribs are oriented radially when viewed in lateral cross section.

50. The apparatus of claim 45, wherein the baffle is a cyclone baffle.

51. The apparatus of claim 1, wherein the second valve element extends in a substantially axial direction when the apparatus is not in use.

* * * * *

(12) INTER PARTES REEXAMINATION CERTIFICATE (903rd)
United States Patent
Gallem et al.

(10) Number: US 7,562,656 C1
(45) Certificate Issued: Jul. 14, 2014

(54) AEROSOL MEDICATION INHALATION SYSTEM

(75) Inventors: Thomas Gallem, München (DE); Kevin Grant Gowanlock, London (CA); Robert Carlton Lynch, Apex, NC (US)

(73) Assignee: Pre Holding, Inc., Midlothian, VA (US)

Reexamination Request:
No. 95/001,216, Oct. 26, 2009

Reexamination Certificate for:
Patent No.: 7,562,656
Issued: Jul. 21, 2009
Appl. No.: 10/943,542
Filed: Sep. 17, 2004

Related U.S. Application Data (63) Continuation of application No. 10/137,007, filed on May 2, 2002, now abandoned.

(51) Int. Cl.
*A61M 11/00* (2006.01)

(52) U.S. Cl.
USPC ............ 128/200.14; 128/200.22; 128/200.17

(58) Field of Classification Search
None
See application file for complete search history.

(56) References Cited

To view the complete listing of prior art documents cited during the proceeding for Reexamination Control Number 95/001,216, please refer to the USPTO's public Patent Application Information Retrieval (PAIR) system under the Display References tab.

*Primary Examiner* — Aaron J. Lewis (57) ABSTRACT

An apparatus for use in conjunction with a metered dose inhaler which includes a novel valve system to aid in the delivery of aerosolized medicament to a subject. The apparatus also includes a novel rotational flow generator to aid in the useable delivery of said medication and avoid its loss either in the apparatus or by non-useful delivery to said subject.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-4, 6-19 and 24-39 are cancelled.

Claims 5, 20 and 51 are determined to be patentable as amended.

Claims 21-23, dependent on an amended claim, are determined to be patentable.

New claim 52 is added and determined to be patentable.

Claims 40-50 were not reexamined.

5. [The apparatus of claim 2,] *An apparatus for aerosol medication delivery, comprising:*
   *a holding chamber having a first and second ends, the first end being adapted to accept a source of aerosol medicament; and*
   *a mouthpiece member provided at the second end of the holding chamber, for delivering aerosol medicament to a subject, the mouthpiece member comprising:*
      *a housing defining a passage through which aerosol medicament can be supplied to a subject and comprising a sidewall in which an opening is formed that opens to the outside of the housing; and*
      *a one-piece valve member comprising a first valve element in fluid communication with the mouthpiece and the holding chamber, the first valve element within the passage to permit delivery of aerosol to a subject during inhalation and blocks the passage during exhalation and a second valve element in fluid communication with the mouthpiece and the opening in the side wall, the second valve element to prevent air from reaching the subject through the opening in the sidewall of the housing during inhalation and permits the flow of air to the outside of the housing from the passage during exhalation,*
   *wherein the first valve element extends axially away from the housing when the apparatus is in a rest position;*
   *wherein the housing defining the passage comprises a delivery member and an adaptor member, the adaptor member is provided at the second end of the holding chamber, and the delivery member is releasably connected to the adaptor member; and*
   wherein the opening in the sidewall is defined by a notch defined in an edge of the adaptor member and a notch defined in an edge of the delivery member.

20. [The apparatus of claim 19,] *An apparatus for aerosol medication delivery, comprising: a holding chamber having a first and second ends, the first end being adapted to accept a source of aerosol medicament; and*
   *a mouthpiece member provided at the second end of the holding chamber, for delivering aerosol medicament to a subject, the mouthpiece member comprising:*
      *a housing defining a passage through which aerosol medicament can be supplied to a subject and comprising a sidewall in which an opening is formed that opens to the outside of the housing; and*
      *a one-piece valve member comprising a first valve element in fluid communication with the mouthpiece and the holding chamber, the first valve element within the passage to permit delivery of aerosol to a subject during inhalation and blocks the passage during exhalation and a second valve element in fluid communication with the mouthpiece and the opening in the side wall, the second valve element to prevent air from reaching the subject through the opening in the sidewall of the housing during inhalation and permits the flow of air to the outside of the housing from the passage during exhalation,*
      *wherein the first valve element extends axially away from the housing when the apparatus is in a rest position;*
   *wherein the housing defining the passage comprises a delivery member and an adaptor member, the adaptor member is provided at the second end of the holding chamber, and the delivery member is releasably connected to the adaptor member;*
   *wherein the adaptor member and the delivery member define first and second opposed surfaces and the valve member is held between the first and second opposed surfaces; and*
   wherein one of the delivery member and the adaptor member comprises a plurality of pins that extend from one of the first and second opposed surfaces and the other of the delivery member and the adaptor member comprises openings for accepting the pins.

51. [The apparatus of claim 1,] *An apparatus for aerosol medication delivery, comprising: a holding chamber having a first and second ends, the first end being adapted to accept a source of aerosol medicament; and*
   *a mouthpiece member provided at the second end of the holding chamber, for delivering aerosol medicament to a subject, the mouthpiece member comprising:*
      *a housing defining a passage through which aerosol medicament can be supplied to a subject and comprising a sidewall in which an opening is formed that opens to the outside of the housing; and*
      *a one-piece valve member comprising a first valve element in fluid communication with the mouthpiece and the holding chamber, the first valve element within the passage to permit delivery of aerosol to a subject during inhalation and blocks the passage during exhalation and a second valve element in fluid communication with the mouthpiece and the opening in the side wall, the second valve element to prevent air from reaching the subject through the opening in the sidewall of the housing during inhalation and permits the flow of air to the outside of the housing from the passage during exhalation,*
   *wherein the first valve element is a duckbill valve extending axially away from the housing when the apparatus is in a rest position;*
   wherein the second valve element extends in a substantially axial direction when the apparatus is not in use.

52. *An apparatus for aerosol medication delivery, comprising: a holding chamber having a first and second ends, the first end being adapted to accept a source of aerosol medicament; and*
   *a mouthpiece member provided at the second end of the holding chamber, for delivering aerosol medicament to a subject, the mouthpiece member comprising:* a housing defining a passage through which aerosol medicament can be supplied to a subject and comprising a sidewall in which an opening is formed that opens to the outside of the housing; and a one-piece valve member comprising a first valve element in fluid communication with the mouthpiece and the holding chamber, the first valve element within the passage to permit delivery of aerosol to a subject during inhalation and blocks the passage during exhalation and a second valve element in fluid communication with the mouthpiece and the opening in the side wall, the second valve element to prevent air from reaching the subject through the opening in the sidewall of the housing during inhalation and permits the flow of air to the outside of the housing from the passage during exhalation, wherein the first valve element is a duckbill valve extending axially away from the housing when the apparatus is in a rest position;

wherein the second valve element comprises a hinged flap extending axially in a direction generally parallel to a length of the holding chamber when the apparatus is in the rest position.

\* \* \* \* \*